(12) United States Patent
Lee et al.

(10) Patent No.: US 11,246,637 B2
(45) Date of Patent: Feb. 15, 2022

(54) STIMULATING TARGETING NEEDLE

(71) Applicant: Alphatec Spine, Inc., Carlsbad, CA (US)

(72) Inventors: James Lee, Carlsbad, CA (US); Graham Witherby, Carlsbad, CA (US)

(73) Assignee: Alphatec Spine, Inc., Carlsbad, CA (US)

( * ) Notice: Subject to any disclaimer, the term of this patent is extended or adjusted under 35 U.S.C. 154(b) by 0 days.

(21) Appl. No.: 16/872,248

(22) Filed: May 11, 2020

(65) Prior Publication Data

US 2021/0346072 A1  Nov. 11, 2021

(51) Int. Cl.
  *A61B 17/86* (2006.01)
  *A61B 17/88* (2006.01)
  *A61B 17/34* (2006.01)
  *A61B 17/00* (2006.01)

(52) U.S. Cl.
  CPC ...... *A61B 17/8819* (2013.01); *A61B 17/3494* (2013.01); *A61B 17/864* (2013.01); *A61B 2017/00411* (2013.01)

(58) Field of Classification Search
  CPC .. A61B 5/4509; A61B 17/864; A61B 17/8819
  See application file for complete search history.

(56) References Cited

U.S. PATENT DOCUMENTS 3,313,293 A * 4/1967 Chesebrough ....... A61N 1/0502
  600/373
3,336,916 A * 8/1967 Edlich ................ A61B 18/1402
  600/431
3,598,108 A * 8/1971 Jamshidi ............ A61B 10/0233
  600/567

(Continued)

FOREIGN PATENT DOCUMENTS

EP  2396072 A1  12/2011
WO  2006029373 A1  3/2006

(Continued)

OTHER PUBLICATIONS

European Patent Office as International Searching Authority, "International Search Report and Written Opinion," International Application No. PCT/US2021/030582, dated Aug. 17, 2021.

(Continued)

*Primary Examiner* — Nicholas W Woodall
(74) *Attorney, Agent, or Firm* — Dentons Durham Jones Pinegar; Sarah W. Matthews

(57) ABSTRACT

A surgical system may include a conductive stylet with a distal end advanceable into bone material and a proximal end coupled to a stylet hub. A handle is non-removably attached to the stylet hub, and removably attachable to an insulative cannula hub. The cannula hub is non-removably attached to a conductive cannula that surrounds the stylet when the handle is attached to the proximal end of the insulative cannula hub. An outer insulative sheath is slideably engaged to insulative cannula hub, and has a radiopaque distal tip. An electrical signal source may be applied to the stylet hub to conduct a pedicle integrity assessment. The handle and stylet may be removed from the cannula assembly, leaving the cannula assembly in place at the surgical site.

19 Claims, 15 Drawing Sheets

(56) References Cited

U.S. PATENT DOCUMENTS

| | | | |
|---|---|---|---|
| 4,655,226 A * | 4/1987 | Lee | A61B 10/025 600/567 |
| 4,892,105 A * | 1/1990 | Prass | A61B 5/276 607/116 |
| 5,196,015 A * | 3/1993 | Neubardt | A61B 17/8875 600/554 |
| 5,335,668 A * | 8/1994 | Nardella | A61B 5/0535 600/547 |
| 5,368,046 A * | 11/1994 | Scarfone | A61B 10/025 600/567 |
| 5,474,558 A * | 12/1995 | Neubardt | A61B 17/8875 600/554 |
| 5,738,114 A | 4/1998 | Edwards | |
| H1905 H | 10/2000 | Hill | |
| 6,129,726 A | 10/2000 | Edwards et al. | |
| 6,159,163 A * | 12/2000 | Strauss | A61N 1/326 600/566 |
| D439,980 S | 4/2001 | Reiley et al. | |
| D449,691 S | 10/2001 | Reiley et al. | |
| 6,337,994 B1 | 1/2002 | Stoianovici et al. | |
| 6,575,919 B1 | 6/2003 | Reiley et al. | |
| 6,829,508 B2 | 12/2004 | Schulman et al. | |
| 7,081,122 B1 | 7/2006 | Reiley et al. | |
| 7,081,123 B2 * | 7/2006 | Merboth | A61B 10/025 600/565 |
| 7,198,625 B1 | 4/2007 | Hui et al. | |
| 7,377,918 B2 | 5/2008 | Amoah | |
| 7,399,306 B2 | 7/2008 | Reiley et al. | |
| 7,445,619 B2 | 11/2008 | Auge, II et al. | |
| 7,643,884 B2 * | 1/2010 | Pond, Jr | A61B 17/1757 607/116 |
| 7,657,308 B2 | 2/2010 | Miles et al. | |
| 7,828,775 B2 | 11/2010 | Okoniewski | |
| 7,842,038 B2 | 11/2010 | Haddock et al. | |
| 7,892,207 B2 | 2/2011 | Simonton | |
| 7,905,884 B2 | 3/2011 | Simonton | |
| 7,918,802 B2 | 4/2011 | Urmey | |
| 7,942,826 B1 | 5/2011 | Scholl et al. | |
| 7,976,542 B1 | 7/2011 | Cosman et al. | |
| 8,088,137 B2 | 1/2012 | Morisseau | |
| 8,167,899 B2 | 5/2012 | Justis et al. | |
| 8,192,443 B2 | 6/2012 | Perez-Cruet | |
| 8,257,358 B2 | 9/2012 | Haddock et al. | |
| 8,374,673 B2 * | 2/2013 | Adcox | A61B 17/1655 600/410 |
| 8,758,383 B2 | 6/2014 | Geist | |
| 8,784,330 B1 | 7/2014 | Scholl et al. | |
| 8,888,780 B2 | 11/2014 | Haddock et al. | |
| 8,974,485 B2 | 3/2015 | Geist et al. | |
| 8,977,367 B2 | 3/2015 | Elahi et al. | |
| 8,986,318 B2 | 3/2015 | Smith | |
| 9,198,674 B2 | 12/2015 | Benson et al. | |
| 9,226,756 B2 | 1/2016 | Teisen et al. | |
| 9,332,973 B2 * | 5/2016 | McWeeney | A61B 10/04 |
| 9,381,024 B2 | 7/2016 | Globerman et al. | |
| 9,421,359 B2 | 8/2016 | Wang et al. | |
| 9,681,889 B1 * | 6/2017 | Greenhalgh | A61B 17/3472 |
| 9,750,508 B1 * | 9/2017 | Barnes | A61B 17/1671 |
| 9,788,843 B2 | 10/2017 | Teisen et al. | |
| 9,968,373 B1 * | 5/2018 | Greenhalgh | A61B 17/3478 |
| 9,999,444 B2 | 6/2018 | Geist et al. | |
| 10,058,350 B2 | 8/2018 | Geist | |
| 10,244,956 B2 | 4/2019 | Kane | |
| 10,556,046 B2 * | 2/2020 | McGillicuddy | A61M 1/86 |
| 10,993,707 B2 * | 5/2021 | McGillicuddy | A61B 10/025 |
| 2002/0049449 A1 * | 4/2002 | Bhatnagar | A61B 17/8816 606/94 |
| 2002/0169471 A1 | 11/2002 | Ferdinand | |
| 2005/0228374 A1 | 10/2005 | Desinger et al. | |
| 2006/0173374 A1 | 8/2006 | Neubardt et al. | |
| 2006/0173521 A1 | 8/2006 | Pond, Jr. et al. | |
| 2006/0217655 A1 | 9/2006 | Vitulio et al. | |
| 2006/0241627 A1 | 10/2006 | Reo | |
| 2006/0276870 A1 | 12/2006 | McGinnis | |
| 2007/0066987 A1 | 3/2007 | Scanlan, Jr. et al. | |
| 2007/0112343 A1 | 5/2007 | Mische et al. | |
| 2007/0197935 A1 | 8/2007 | Reiley et al. | |
| 2007/0270896 A1 | 11/2007 | Perez-Cruet | |
| 2008/0132979 A1 | 6/2008 | Gerber | |
| 2008/0140022 A1 | 6/2008 | Pond et al. | |
| 2008/0161845 A1 | 7/2008 | Murakami et al. | |
| 2009/0036756 A1 | 2/2009 | Pradeep et al. | |
| 2009/0118727 A1 | 5/2009 | Pearson et al. | |
| 2009/0157091 A1 | 6/2009 | Buysman | |
| 2009/0187222 A1 | 7/2009 | Barker | |
| 2010/0087755 A1 | 4/2010 | Boezaart | |
| 2010/0256517 A1 | 10/2010 | Neubardt et al. | |
| 2010/0312103 A1 | 12/2010 | Gorek et al. | |
| 2011/0004207 A1 | 1/2011 | Wallace et al. | |
| 2011/0105876 A1 | 5/2011 | Zhang | |
| 2012/0010643 A1 | 1/2012 | Shao | |
| 2012/0150063 A1 | 6/2012 | Rea | |
| 2012/0197320 A1 | 8/2012 | Bereczki | |
| 2012/0215217 A1 | 8/2012 | Horner et al. | |
| 2012/0226301 A1 * | 9/2012 | Geist | A61B 17/3472 606/172 |
| 2013/0150752 A1 * | 6/2013 | Swann | A61M 1/67 600/567 |
| 2013/0184551 A1 | 7/2013 | Paganelli et al. | |
| 2015/0100077 A1 | 4/2015 | Geist | |
| 2016/0128599 A1 | 5/2016 | Rea | |
| 2016/0262731 A1 | 9/2016 | Kliot et al. | |
| 2016/0310751 A1 | 10/2016 | Bonde et al. | |
| 2017/0196601 A1 | 7/2017 | Koenig et al. | |
| 2018/0035906 A1 | 2/2018 | Scholl et al. | |
| 2018/0103981 A1 | 4/2018 | Lopez | |
| 2018/0256201 A1 | 9/2018 | Greenhalgh et al. | |
| 2018/0256202 A1 | 9/2018 | Greenhalgh et al. | |
| 2018/0360489 A1 | 12/2018 | Geist | |
| 2018/0360648 A1 | 12/2018 | Press | |
| 2019/0110705 A1 | 4/2019 | Sakai et al. | |
| 2021/0113239 A1 * | 4/2021 | Donovan | A61B 17/1633 |

FOREIGN PATENT DOCUMENTS

| | | |
|---|---|---|
| WO | 2009046414 A1 | 4/2009 |
| WO | 2009154308 A1 | 12/2009 |
| WO | 2010078510 A2 | 7/2010 |

OTHER PUBLICATIONS

SurGenTec ALARA Needle Video available at https://www.surgentec.com/alara-neuro-access-kit/ and at https://vimeo.com/user104331883, available at least as early as Oct. 1, 2019.

* cited by examiner

STIMULATING TARGETING NEEDLE

TECHNICAL FIELD

The present disclosure relates generally to a surgical instrument which may be used in spinal surgery. More specifically, and without limitation, the present disclosure relates to a device which may be advanced into bone and connected to a source of electrical stimulus to perform a pedicle integrity assessment.

RELATED ART

Spinal surgery may be used to treat various conditions, such as degenerative disc disease, recurrent disc herniation, spinal instability, spondylolisthesis, pseudo arthrosis, osteomyelitis/discitis, post-laminectomy syndrome and trauma. Bone anchors are often used in spinal surgery to secure a spinal fixation element to one or more vertebrae to rigidly or dynamically stabilize the spine.

In a conventional procedure for coupling a bone anchor to bone, access to the bone is obtained, for example by forming a skin incision and resecting soft tissue disposed over the bone or by using a minimally-invasive technique. The surgeon then drives an insertion needle with a stylet disposed therein into the bone to establish the trajectory for a bone opening. Next, the stylet is removed and a guidewire is inserted through the needle. The needle is then withdrawn over the guidewire, leaving the guidewire in place. A cannulated tap is then advanced over the guidewire and driven into the bone to enlarge the bone opening into a pilot hole for the bone anchor. Thereafter, the tap is withdrawn over the guidewire, again leaving the guidewire in place within the bone opening. A cannulated bone anchor is then advanced over the guidewire and driven into the bone opening. Finally, the guidewire is removed and one or more fixation elements are coupled to the bone anchor.

Placement of the pedicle screw must be done in this process with a great deal of care to prevent damage to neural structures close to the bony pedicle. If a pedicle is breached, cracked, or otherwise compromised, the patient may experience pain or neurologic deficit due to unwanted contact between the pedicle screw and an exiting nerve.

Intraoperative confirmation of secure screw placement can be obtained using imaging, but neural integrity must be separately checked. Moreover, completely depending on imaging may not be appropriate, especially when proper anatomy cannot be visualized. Therefore, neurophysiological electrical pedicle testing can be a useful aid in the detection of malpostioned pedicle screw tracts. Electrical pedicle testing may allow for immediate repositioning of screws.

Electrical pedicle testing utilizes the insulating characteristics of bone (specifically, that of the walls of the pedicle) and the conductivity of the exiting nerve roots themselves. If a wall of the pedicle is breached, a stimulation signal applied to the pedicle screw and/or the pilot hole will cause the various muscle groups coupled to the exiting nerve roots to contract. If the pedicle wall has not been breached, the insulating nature of the pedicle will prevent the stimulation signal from innervating the given nerve roots such that the associated muscle groups will not twitch.

To achieve successful placement of pedicle screws, there is a need for a surgical tool that can accurately perform pedicle integrity assessments intra-operatively. The surgical device may also be relatively simple in use, and provide visual indicators to assist the surgeon intra-operatively.

SUMMARY

According to one aspect, a surgical tool system is disclosed that may include a conductive stylet with a distal end advanceable into bone material. The proximal end may be attached to a stylet hub. A handle is non-removably attached to the stylet hub, and the handle, stylet, and stylet hub form a handle assembly that may be removably attachable to the proximal end of a cannula assembly. The cannula assembly may include an insulative cannula hub non-removably attached to a cannula. The cannula may surround the stylet when the handle assembly is inserted into the cannula assembly. An outer, elongated insulative sheath may be slideably engaged to the insulative cannula hub. The outer sheath may also be provided with a radiopaque tip.

According to another aspect, the handle may have a void extending longitudinally through the proximal end and the distal end, with the conductive stylet hub passing through the void in the proximal end and distal end. A proximal end of the conductive stylet hub may be exposed through the proximal end of the handle, to allow a surgeon to apply pressure to the stylet hub to drive the stylet into bone, while maintaining the integrity of the handle. The handle further may also include a geometry indicator at a proximal end of the handle.

According to another aspect, the conductive stylet hub has a diameter at least as large as the cannula diameter. In some configurations, the handle includes a distal connecting portion, the conductive stylet hub receivable within a longitudinal void extending through the proximal gripping portion and distal connecting portion. In yet other configurations, the handle includes a projection on the distal connecting portion with a laterally extending flange. The cannula hub includes a proximal void with one or more slots, the projection on the distal connecting portion of the handle receivable within the proximal void and the laterally extending flange receivable within the one or more slots.

In some configurations, the conductive stylet is integral to the handle. Similarly, the cannula may be integral to the cannula hub. The outer sheath may include a front half and a back half, the front half and back half ultrasonically welded together along a longitudinal axis of the outer, elongated insulative sheath. The outer sheath may also include markings indicating a depth of penetration of the surgical tool system.

According to another aspect, the insulative cannula hub may include a longitudinal channel having a first groove and a second groove, and the outer, elongated insulative sheath may include an extension slideable within the longitudinal channel. The cannula hub may also include markings indicating a length of the conductive stylet extending beyond the outer, elongated insulative sheath.

According to another aspect, the conductive stylet hub may be coupled to an electrical source to transmit an electrical current from the electrical source to the conductive stylet hub to conduct a pedicle integrity assessment.

Other aspects of the disclosed subject matter, as well as features and advantages of various aspects of the disclosed subject matter, should be apparent to those of ordinary skill in the art through consideration of the ensuing description, the accompanying drawings, and the appended claims.

BRIEF DESCRIPTION OF DRAWINGS

The following drawings illustrate what are currently considered to be specific representative configurations for carrying out the disclosed subject matter and are not limiting as to embodiments which may be made in accordance with this disclosure. The components in the drawings are not necessarily to scale relative to each other. Like reference numerals designate corresponding parts throughout the several views.

DETAILED DESCRIPTION

Hereinafter, exemplary embodiments of the present disclosure will be described in detail with reference to the accompanying drawings. Advantages and features of the present disclosure and methods accomplishing them will become apparent from the following description of exemplary embodiments with reference to the accompanying drawings. Various aspects discussed in reference to one drawing may be present and/or used in conjunction with the embodiment shown in another drawing, and each element shown in multiple drawings may be discussed only once.

Reference in the specification to "one configuration," "one embodiment," "a configuration," or "an embodiment" means that a particular feature, structure, or characteristic described in connection with the configuration is included in at least one configuration, but it is not a requirement that such feature, structure, or characteristic be present in any particular configuration unless expressly set forth in the claims as being present. The appearances of the phrase "in one configuration" in various places may not necessarily limit the inclusion of a particular element of the invention to a single configuration, rather the element may be included in other or all configurations discussed herein.

The described features, structures, or characteristics of configurations of the disclosed subject matter may be combined in any suitable manner in one or more configurations. As used in this specification and the appended claims, singular forms such as "a," "an," and "the" may include the plural unless the context clearly dictates otherwise. Thus, for example, reference to "a spring" may include one or more of such springs, and reference to "the stylet" may include reference to one or more of such stylets. Structural elements, compositional elements, and/or materials may be presented in a common list for convenience. However, these lists should be construed as though each member of the list is individually identified as a separate and unique member.

Certain components of the surgical tool described herein will be described as being coupled or connected to one another, and such connections and couplings may be achieved in any suitable manner. Additionally, such components may be integrated with one another or distributed in any suitable fashion.

Figure 1:
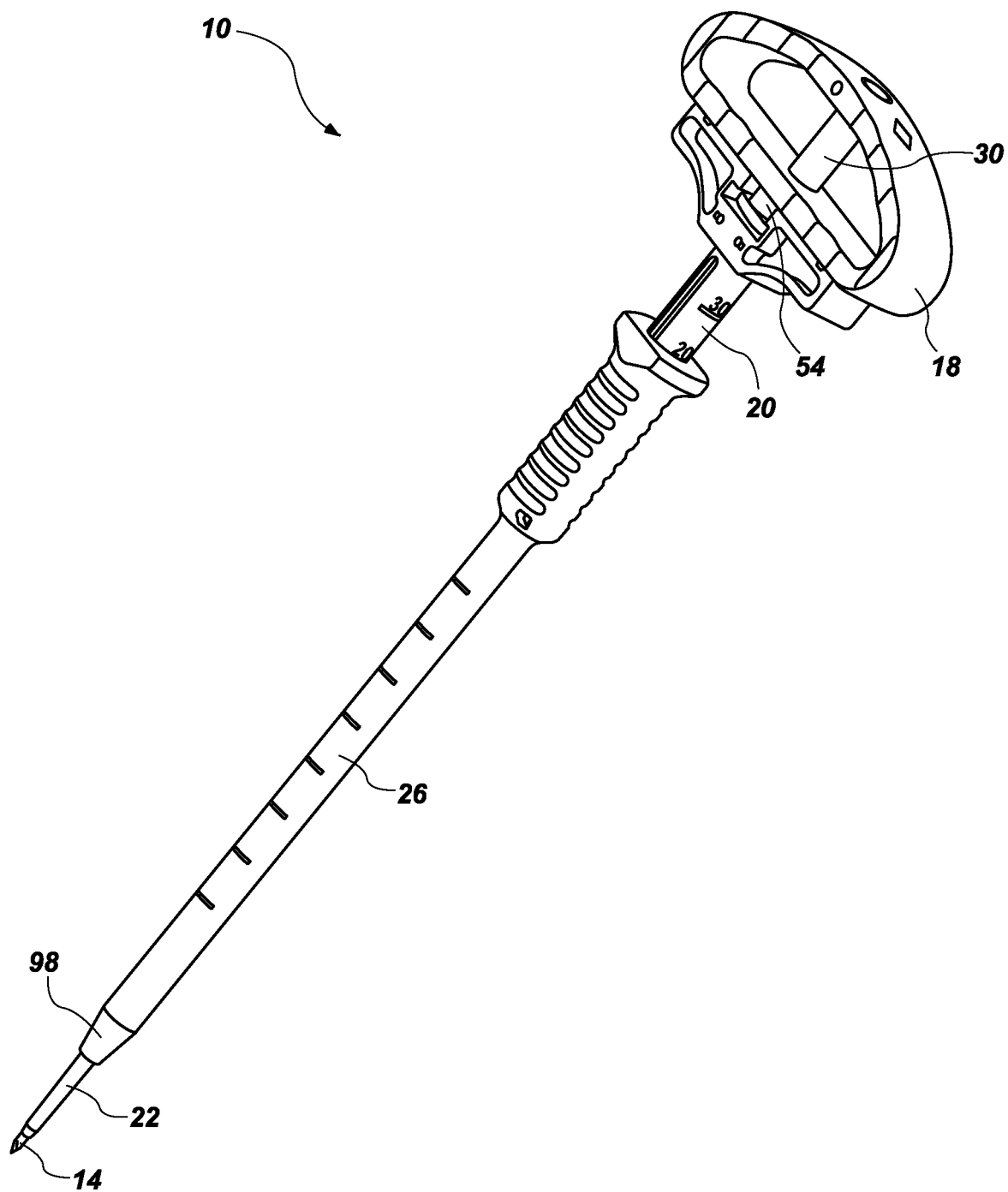
FIG. 1 is a perspective view of an example of a surgical device system as described herein.
Figure 2:
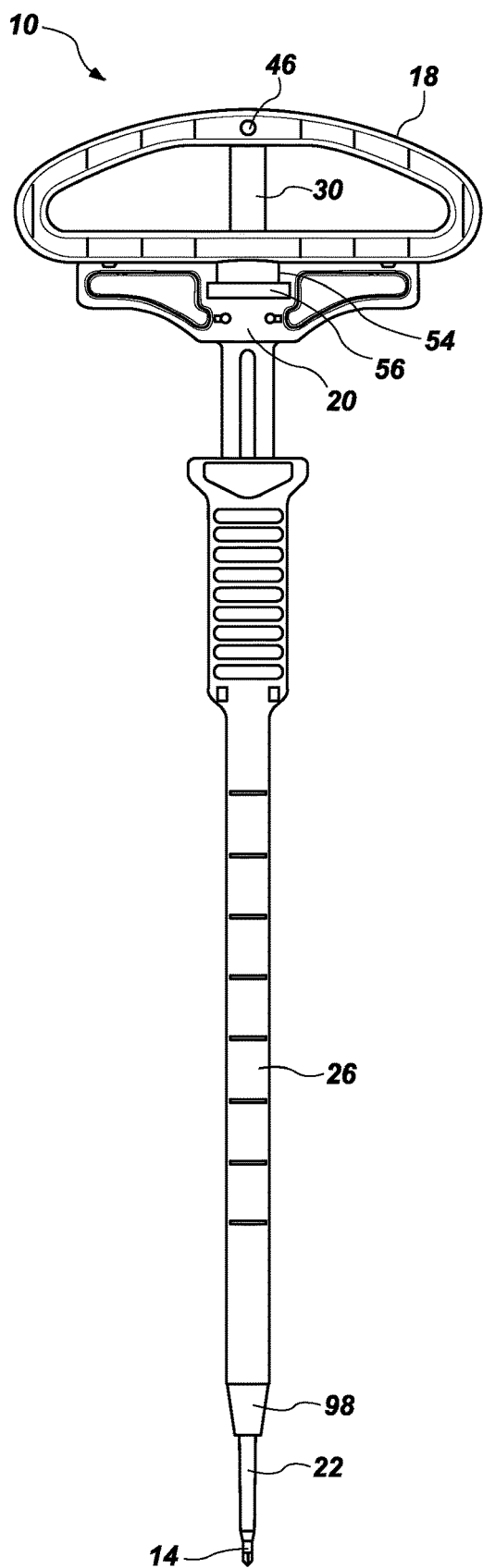
FIG. 2 is a front view of the surgical device system of FIG. 1.
Figure 3:
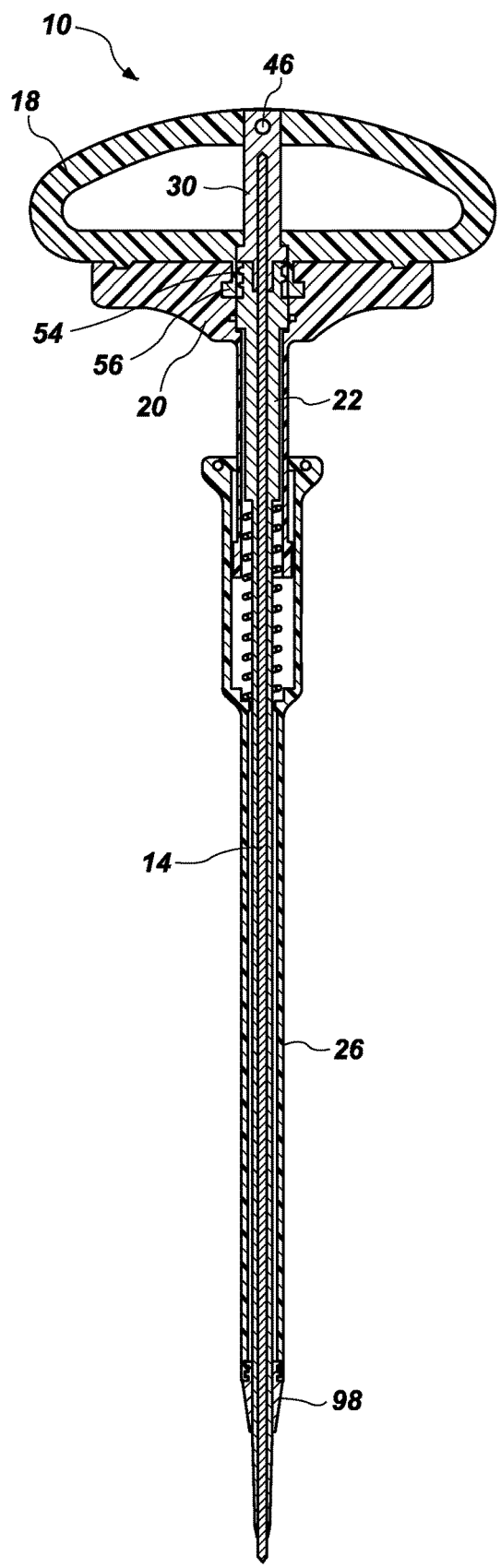
FIG. 3 is a cross-sectional front view of the surgical device system of claim 1.

This disclosure generally relates to a surgical tool and surgical tool system that may be used in spinal surgical procedures to form a pilot hole and conduct a pedicle integrity assessment. One particular embodiment of the present disclosure is shown and described in a surgical tool 10 as shown in FIGS. 1-3. The surgical tool 10 may generally include a stylet 14, a handle 18, a cannula hub 20, a cannula 22, and an insulative sheath 26. The stylet 14 and handle 18 are typically non-removably connected and form the handle assembly 35. The cannula hub 20, cannula 22, and insulative sheath 26 are also typically non-removably connected and form the cannula assembly 65.

Figure 4:
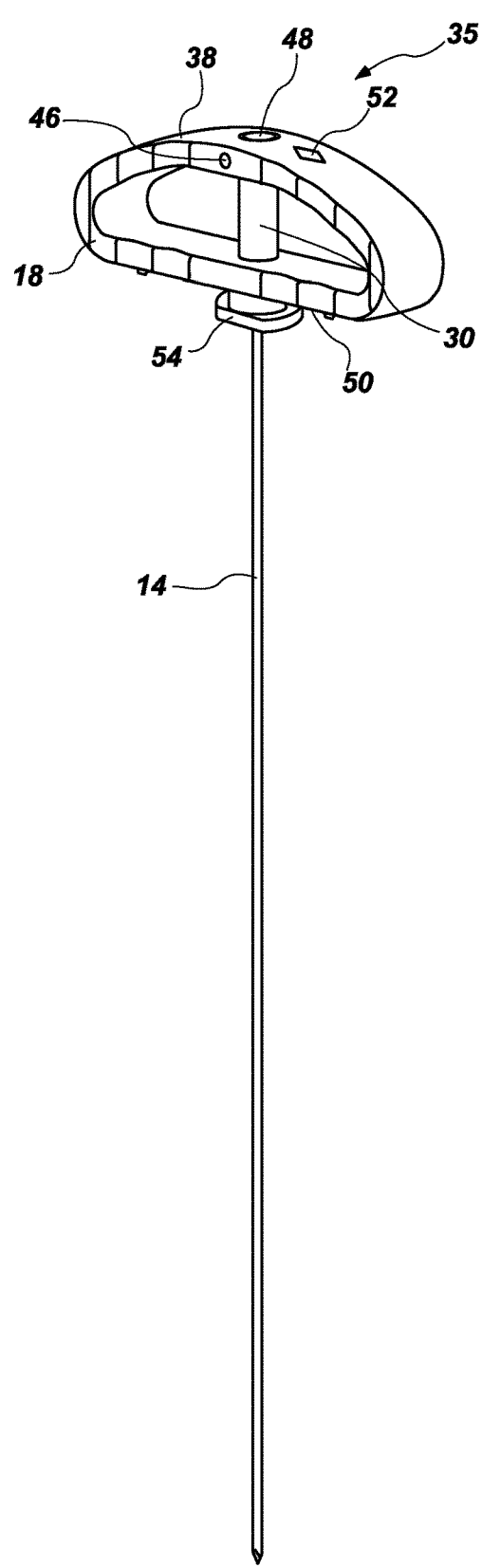
FIG. 4 is a perspective view of a handle assembly forming part of the surgical device system of FIG. 1.
Figure 5:
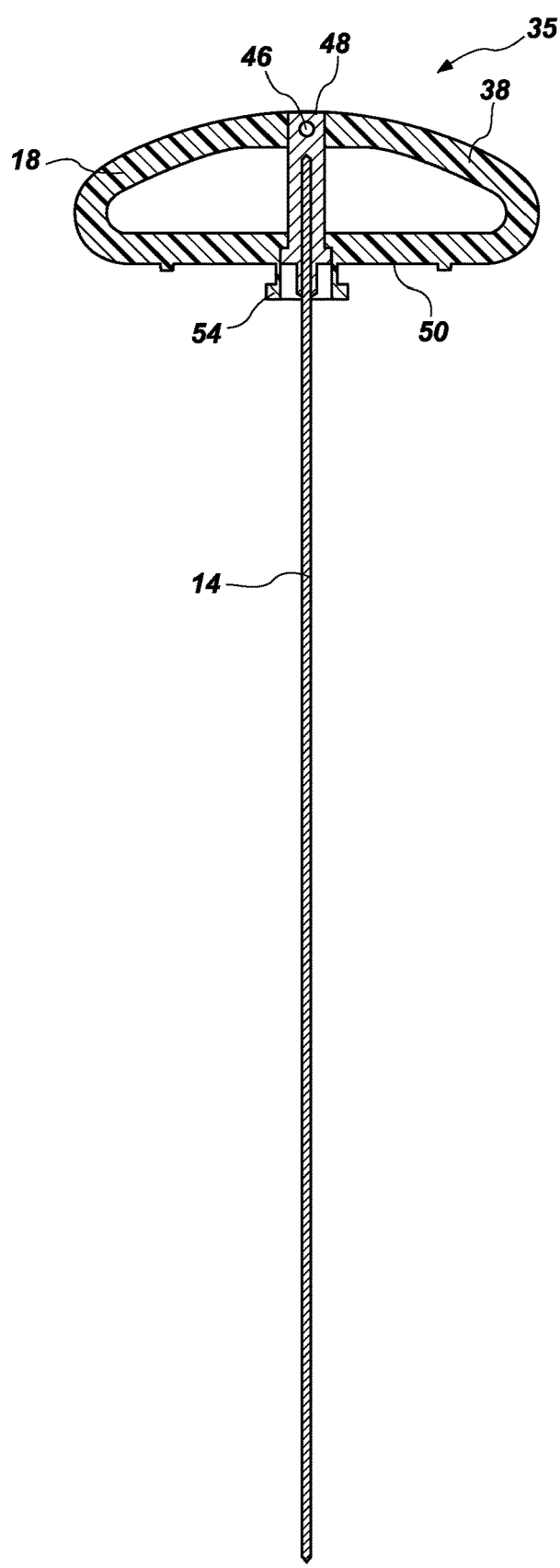
FIG. 5 is a cross-sectional view of the handle assembly of FIG. 4.
Figure 6:
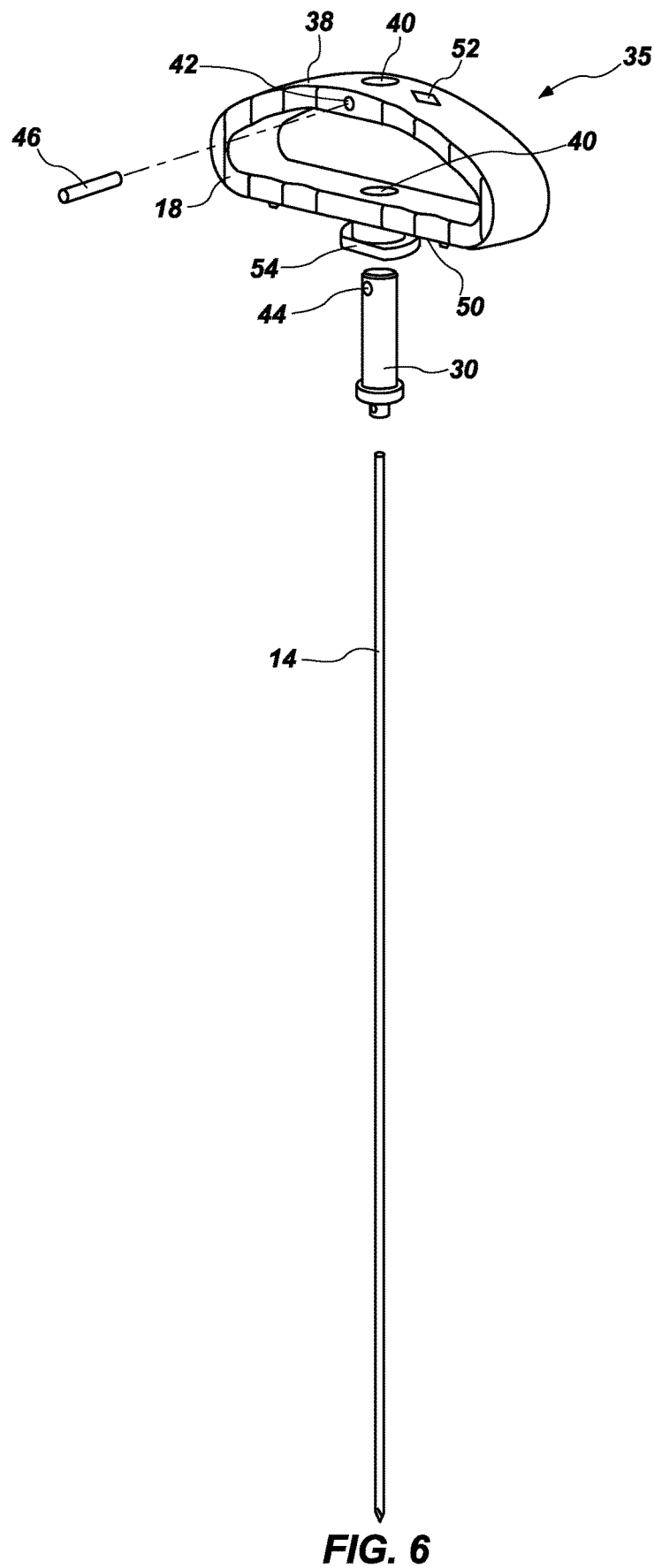
FIG. 6 is an exploded perspective view of the handle assembly of FIG. 4.

Turning to FIGS. 4-6, the handle assembly 35, including stylet 14 is shown. The stylet 14 is typically formed of a conductive material and comprises a shaft with a distal end that can be driven into bone material. The proximal end of the stylet may include a stylet hub 30, which is also typically formed of a conductive material. The stylet hub 30 surrounds the proximal end of the stylet 14 and is in electrical communication with the stylet 14, as described in more detail below, to allow the surgical tool to be used to perform a pedicle integrity assessment during formation of a pilot hole. Typically, the stylet hub 30 and stylet 14 are non-removably connected to the handle 18, and the entire handle assembly 35 may be removably connected to the cannula 22 via the cannula hub 20 as described below. The surgical tool 10 may be used to drive the stylet 14 into bone at a target site, perform a pedicle integrity assessment via the conductive stylet, and the handle assembly 35 may be removed from the cannula assembly 65, with the cannula 22 remaining in place at the surgical site.

The stylet 14 and the stylet hub 30 may be connected or formed of an integral piece. The stylet 14 and stylet hub 30 may be non-removably attached to the handle 18. As shown in FIGS. 4-6, the stylet 14, stylet hub 30, and the handle 18 form the handle assembly 35 and are non-removably connected to each other. In other configurations, the stylet 14, stylet hub 30, and handle 18 may be removably connected. The stylet 14, stylet hub 30, and handle 18 may be secured to each other in various suitable ways. For example, as shown in FIG. 6, the handle 18 may include a proximal gripping portion 38 and an aperture 40 extending longitudinally therethrough for engaging the stylet hub 30. The gripping portion 38 may allow the surgeon to have a place to grip, and also may allow the stylet hub 30 to be relatively exposed, for easy attachment of a device to do a pedicle integrity assessment as described in more detail below.

The aperture 40 of the handle may be sized to closely fit the stylet hub 30. The stylet hub 30 and the handle 18 may also each have an aperture (aperture 42 of handle 18 and aperture 44 of stylet hub 30, seen most clearly in the exploded view in FIG. 6), extending from the front side to the back side. A cylindrical cross-pin 46 may be positioned to extend through the apertures 42 and 44 to further connect the stylet hub 30 and the handle 18. The cross-pin 46 may be press-fit through the corresponding apertures 42 and 44 of the handle 18 and stylet hub 30 to non-removably secure the stylet hub 30 to the handle 18. The illustrated embodiment shows the cross-pin 46 press-fit into the apertures 42 and 44, but any suitable method of securing the cross-pin 46 may be used, and other methods of non-removably or removably attaching the handle 18 to the stylet hub 30 may be used. In some configurations, handle 18 is overmolded onto stylet hub 30, thereby requiring no cross-pins.

In some configurations, the proximal end 48 of the stylet hub 30 may extend through to the proximal gripping portion 38 of the handle such that the proximal end 48 of the stylet hub 30 is exposed on the proximal side of the handle 18. This may allow a surgeon to apply pressure directly to the proximal end 48 of the stylet hub 30, for example by hammering directly onto the proximal end 48 of stylet hub 30, while preserving the integrity of the handle 18. In other configurations, the stylet hub 30 need not extend through to the proximal side 50 of the handle 18. Optionally, the proximal side 50 of the handle 18 may include a geometry indicator 52 that shows the geometry of the tip of the stylet. Surgeons may use stylets having various tip geometries, and with the stylet 14 integral to the handle 18, the stylet geometry may be printed or otherwise indicted on the handle 18, such as at the proximal side 50 of the handle 18, to easily verify to the surgeon the type of stylet tip being used without the need for the surgeon to have a visual on the stylet tip. Various types of tips may be used and provided with geometry indicators, such as a bevel tip, a diamond tip, etc.

The handle assembly 35, including the stylet 14, stylet hub 30, and handle 18, may be removably attachable to the proximal end of the cannula hub 20. This removable connection may be any suitable removable connection. For example, a lockingly mateable connection may be used, such as mating slots and tabs or any other suitable coupling element. The handle 18 may include a projection 54 on its distal side 50, with a flange 56 extending laterally outwardly on the right and left sides from the base of the distal projection 54. The proximal end of the cannula hub 20 includes a void 58 sized to receive the distal projection 54 of the handle 18, and slots 60, 61 sized to receive the flange 56 of the distal projection of the handle.

Figure 7:
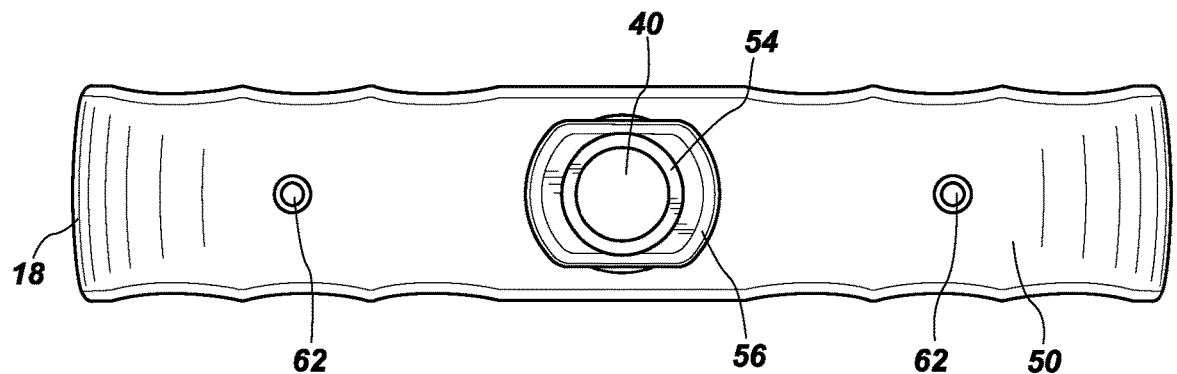
FIG. 7 is a bottom view of the handle forming part of the surgical device system of FIG. 1.
Figure 8:
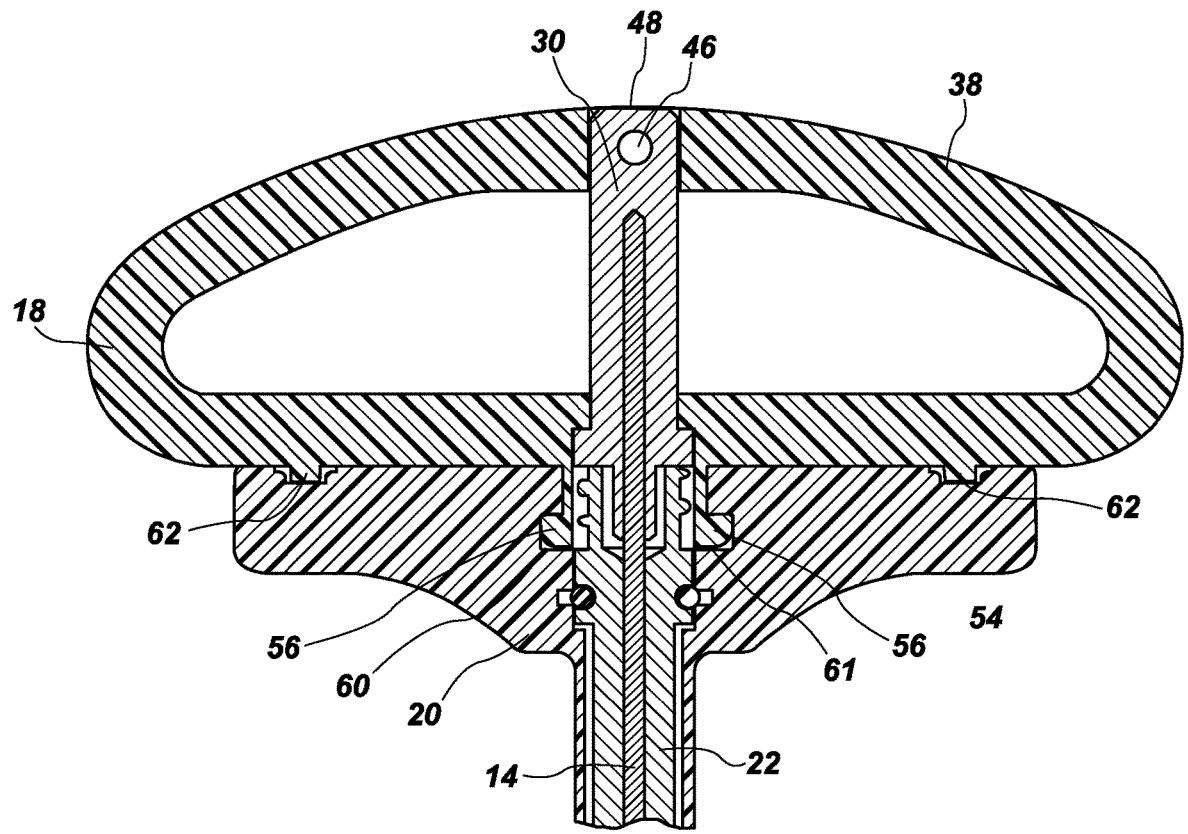
FIG. 8 is an enlarged partial cross-sectional view of the proximal portion of the surgical device system of FIG. 1.

Because the flange 56 extends laterally from the left and right sides (but not the front and back sides), the base of the projection 54 has a narrow side from the front to back, and a wider side comprising the flange 56 from the left to right (as seen in bottom view of handle of FIG. 7). This allows the handle 18 (or, typically, the entire handle assembly 35) to be turned perpendicularly with respect to the cannula hub 20, the narrow side of the projection 54 to be inserted into a void 58 at the proximal end of the cannula hub 20, and the handle assembly 35 then turned 90 degrees, or parallel with the cannula hub 20, as described in greater detail below.

Figure 9:
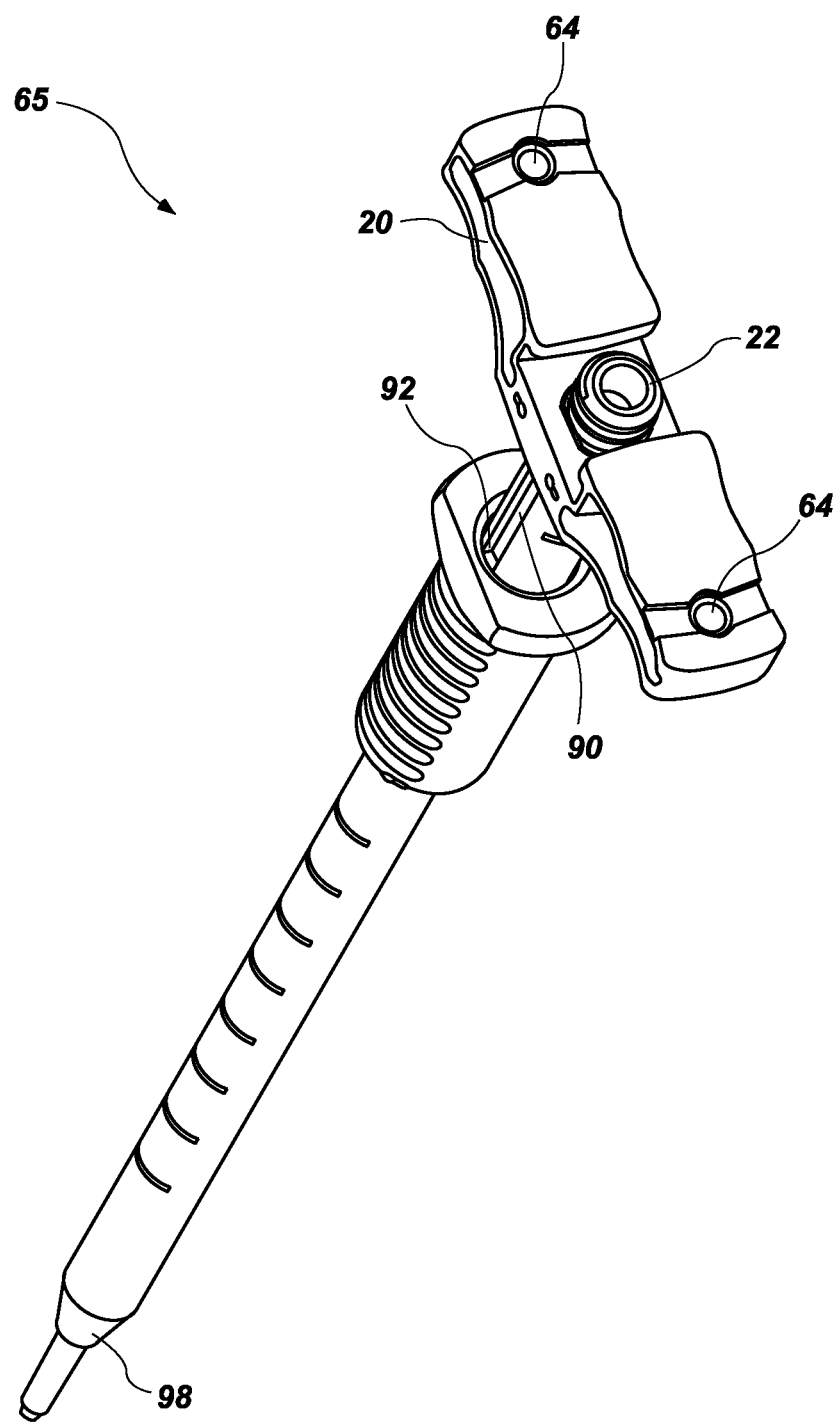
FIG. 9 is a perspective view of the cannula assembly forming part of the surgical device system of FIG. 1.
Figure 10:
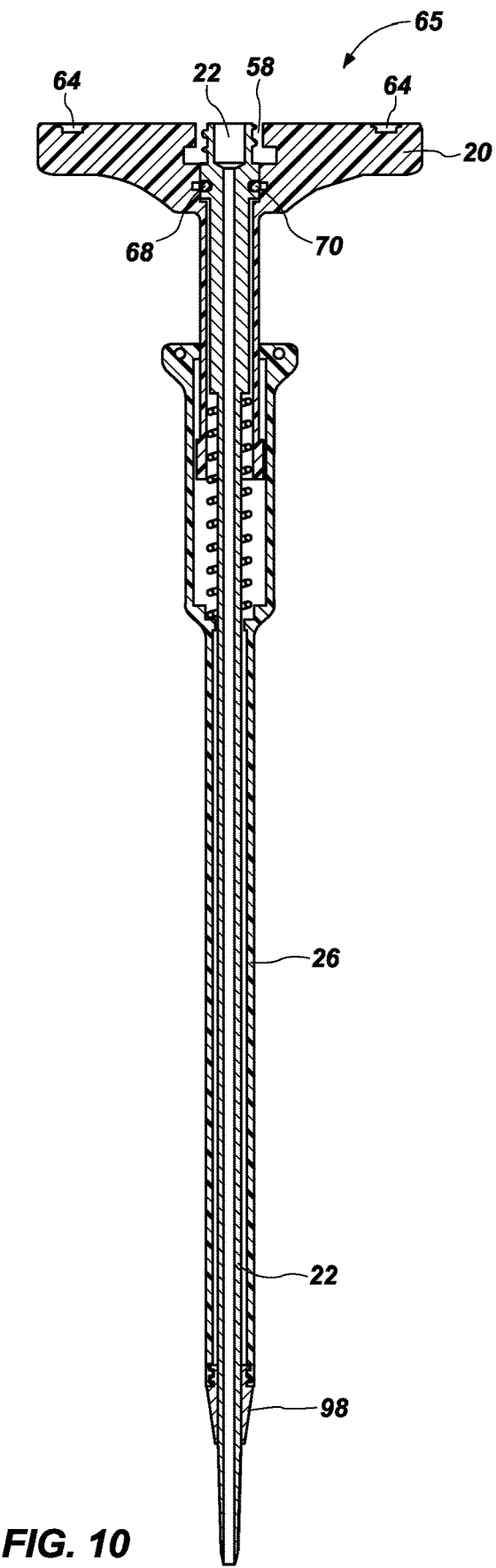
FIG. 10 is a cross-sectional view of the cannula assembly of FIG. 9.

Turning now to the cannula assembly 65, FIGS. 9-10 show an example of a cannula assembly 65, including the cannula hub 20, cannula 22, and insulative sheath 26. The cannula 22 includes a hollow interior, and as shown is formed of a conductive material. In other configurations, the cannula 22 may be formed of insulative material and/or conductive material. The cannula 22 may surround the conductive stylet 14 when the handle assembly 35 is attached to the proximal end of the insulative cannula hub 20. In the configuration depicted in FIG. 11, the cannula 22 has a wider diameter towards a proximal end of the cannula, and a narrower diameter towards the distal end of the cannula. The outer diameter and/or length of the cannula 22 may vary, or a cannula 22 having a single, uniform diameter may also be used.

In some configurations, the cannula 22 has a smaller diameter than the diameter of the stylet hub 30. Configurations with a wider diameter towards a proximal end of the cannula 22, in conjunction with the stylet hub 30 having a diameter at least as large as the proximal cannula diameter, may allow an effective transfer of force from the stylet hub 30 to the cannula 22. For example, when the surgeon hammers on the proximal end 48 of the stylet hub 30 to drive the surgical instrument into bone, the force may be applied not only to the stylet 14 through the stylet hub 30, but also transferred to the cannula 22.

The cannula 22 may be removably or non-removably connected to the cannula hub 20. As explained in detail below, the cannula hub 20 enables the cannula 22 to be easily connected to the handle assembly 35. The cannula hub 20 may be connected to the cannula 22 in any suitable manner and in the exemplary configuration shown in FIG. 10, the cannula hub 20 is non-removably attached to the cannula 22 via two cross-pins 68, 70 that pass through corresponding voids in the cannula hub 20 and cannula 22.

Figure 11:
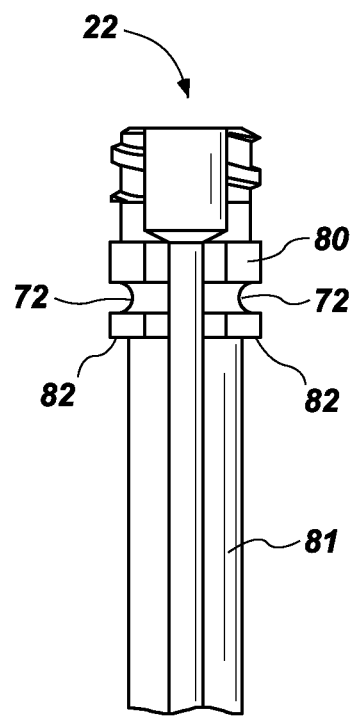
FIG. 11 is a cross-sectional view of a proximal end of a cannula forming part of the cannula assembly of FIG. 9.
Figure 12:
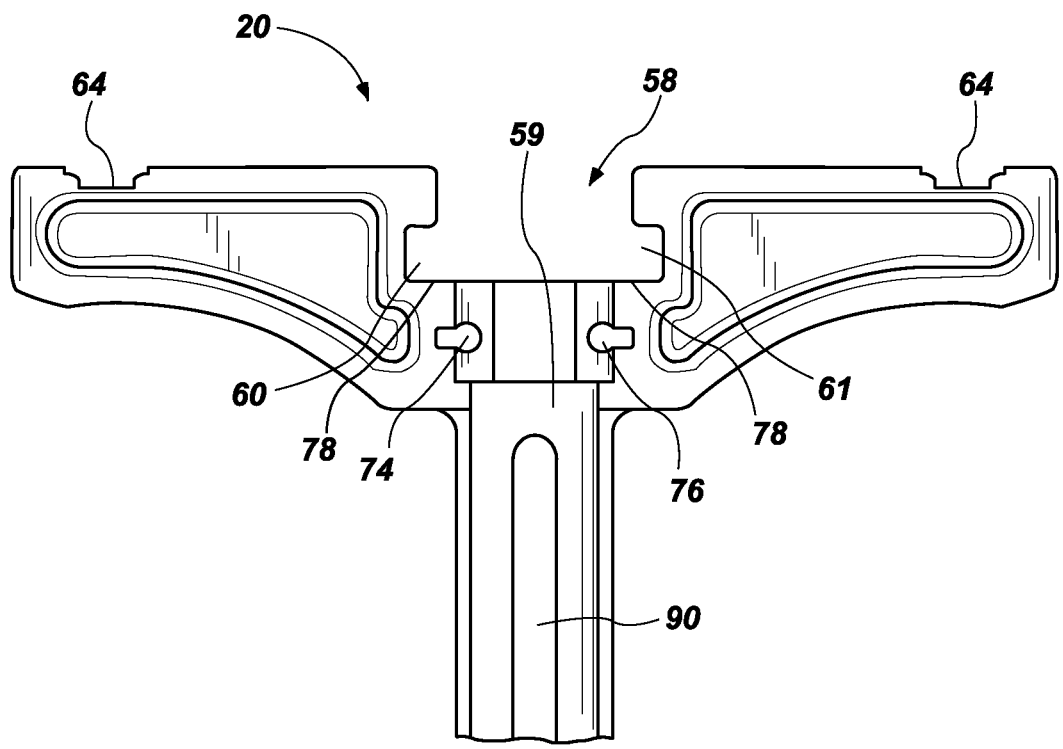
FIG. 12 is a cross-sectional view of a proximal end of a cannula hub forming part of the cannula assembly of FIG. 9.

FIG. 11 shows a partial cross-sectional view of the cannula 22, and FIG. 12 shows a partial cross-sectional view of the cannula hub 20. Cylindrical cross-pins 68, 70 may extend through apertures 74, 76 (FIG. 12) of the cannula hub 20 from the front side to the back side, to permanently attach the cannula hub 20 and cannula 22. The cross-pins may also pass through a void or notch of the cannula 22. As seen in FIG. 11, the outer circumference of the cannula 22 may include a notch 72 in the proximal end that is sized to receive the cross-pins 68, 70. The cross-pins 68, 70 may be press-fit through the corresponding apertures 74, 76 of the cannula hub 20 and notch 72 of the cannula 22 to non-removably secure the cannula hub 20 to the cannula 22. The illustrated embodiment shows the cross-pins 68, 70 press-fit into the apertures 74, 76, but any suitable method of securing the cross-pins 68, 70 may be used, and other methods of non-removably or removably attaching the cannula 22 and cannula hub 20 may be used. In some configurations, cannula hub 20 is overmolded onto a proximal portion of cannula 22, thereby requiring no cross-pins.

The cannula hub 20 and cannula 22 may be further shaped to encourage attachment to each other. For example, as seen in FIG. 12, the cannula hub 20 may have a wider, proximal void 58 shaped to fit the wider, proximal end of the cannula 22, and a narrower, distal void 59 to fit the narrower, distal end of the cannula 22. A shoulder 78 is formed between the wider 58 and narrower 59 voids. The cannula 22 (FIG. 11) may be similarly shaped with a proximal portion 80 that fits into the wider, proximal void 58 of the cannula hub 20, and a narrower distal portion 81 that fits into the narrower, distal void 59 of the cannula 22. A ledge 82 is formed between the wider, proximal portion 80 and the narrower distal portion 81. The ledge 82 engages the shoulder 78 of the cannula hub 20.

The cannula hub 20 may be formed of insulative material. By forming the cannula hub 20 and other portions of the surgical tool 10 of insulative material, it may prevent shunting of the electricity to sites other than the pilot hole.

The cannula hub 20 may also be provided with depth markings 104 (FIG. 13) to allow the surgeon to have a visual on the depth of the cannula 22 in the operation site. The markings on the insulative cannula hub indicate the length of the conductive stylet 14 extending beyond the insulative sheath 26.

The cannula assembly 65 may further comprise an outer, elongated sheath 26. The outer sheath 26 may, similarly to the cannula hub 20, be formed of insulative materials. In some configurations, and as shown in FIG. 9, the outer sheath 26 is slideably engaged with the cannula hub 20. In other configurations the outer sheath 26 may not move relative to the cannula hub 20. In yet other configurations the insulative sheath 26 may have a distal position where it covers the distal tip of the stylet 14, and a proximal position where the tip of the stylet is exposed. A slideable engagement between the outer sheath 26 and the cannula hub 20/cannula 22 assembly may allow the outer sheath to retract as the cannula 22 enters bone.

Figure 14:
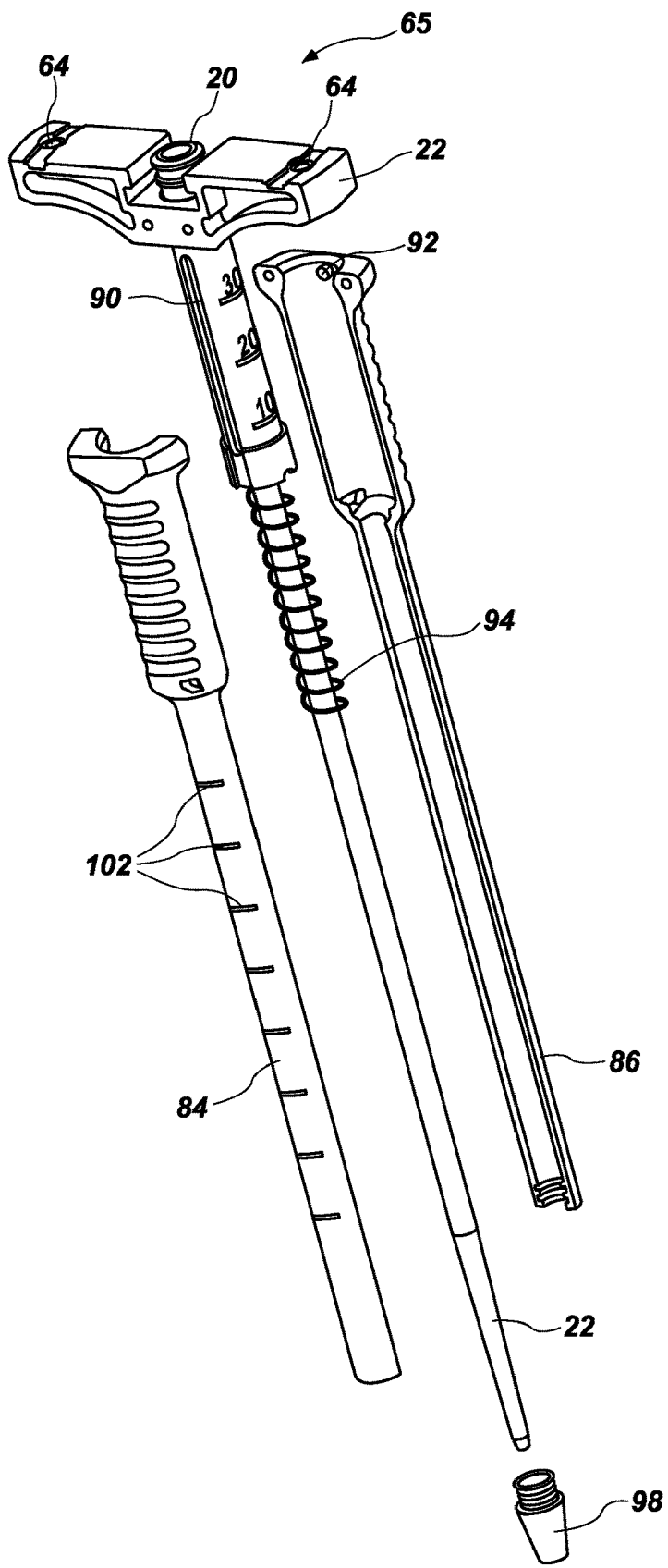
FIG. 14 is an exploded view of the cannula assembly of FIG. 9.

As best seen in FIGS. 9 and 14, the cannula hub 20 may have one or more longitudinal channels 90 and the outer sheath 26 may have corresponding projections 92 slideable within the longitudinal slots 90. In some configurations, one or more grooves or notches may also be provided within the longitudinal slot 90 of the cannula hub 20 to hold the cannula hub 20 in a predetermined position with respect to the outer sheath 26. A spring 94 may also be provided to bias the cannula hub 20 in a position with respect to the outer sheath 26, such as to bias the cannula hub 20 in an extended position.

Figure 13:
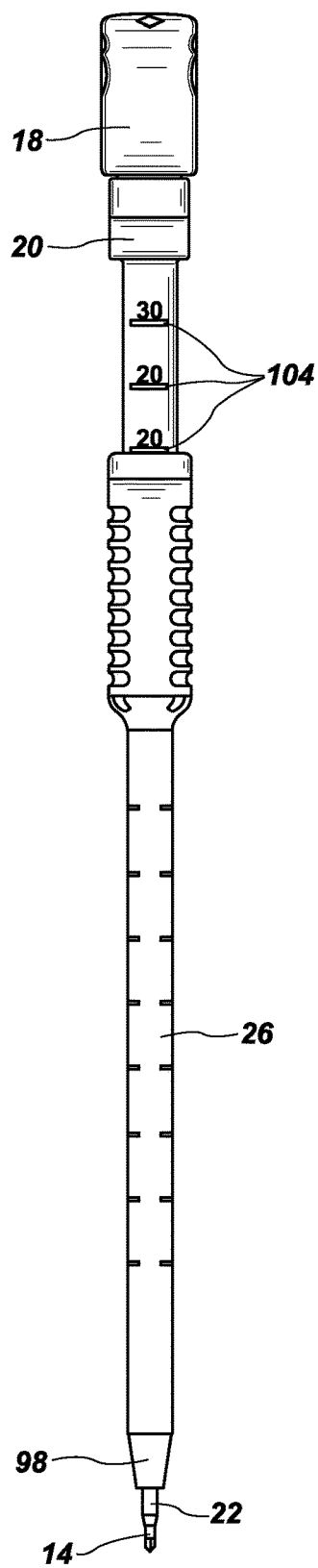
FIG. 13 is a side view of the surgical device system of claim 1.

The sheath 26 may further include a distal tip 98. As shown in FIGS. 13 and 14, the distal tip 98 is formed of radiopaque material. The distal tip 98 may be formed of other suitable materials as desired. By providing a radiopaque distal tip 98, the distal tip 98 of the sheath 26 and location of the distal end of the cannula 22 may be more easily viewed via x-ray. The sheath 26 may also include one or more visual depth indicator markings 102. In use, these markings can tell the surgeon the depth of the instrument from the skin of the patient down to the bone.

Figure 15:
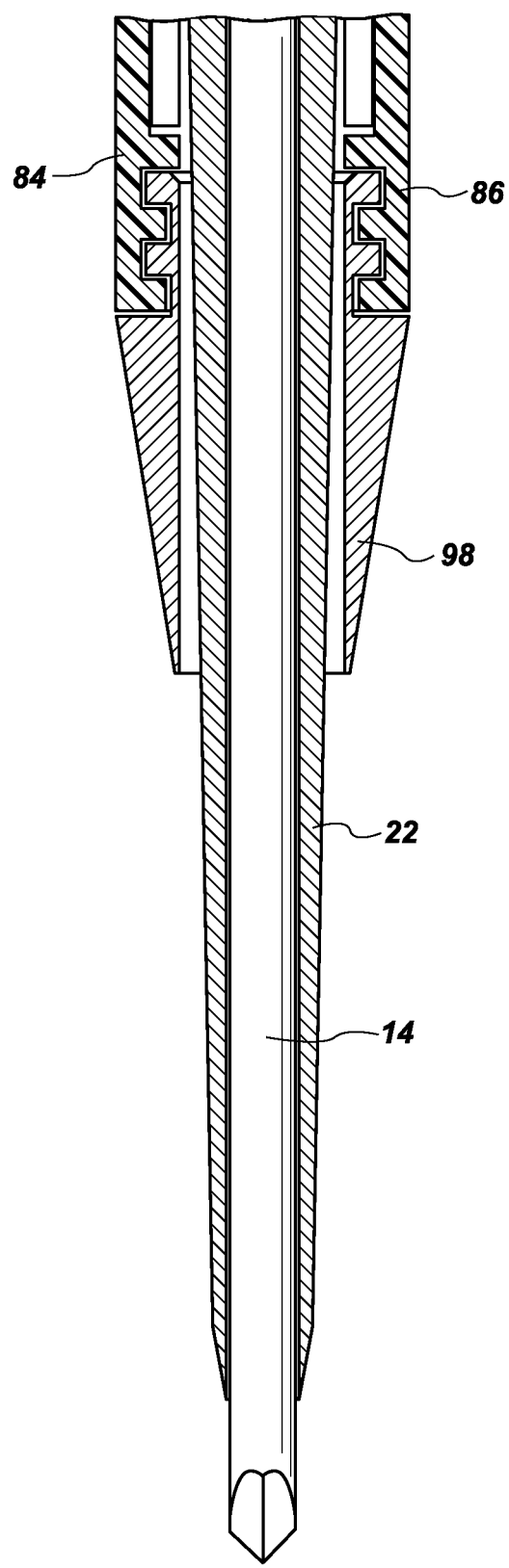
FIG. 15 is a cross-sectional view of the distal end of the cannula assembly of FIG. 9.

The outer sheath 26 may be formed in any suitable manner. For example, the insulative outer sheath 26 sheath may be comprised of a front half 84 and a rear half 86 (FIG. 14). After the cannula 22 and cannula hub 20 are non-removably attached to each other, with the optional spring 94 in place around the cannula 22, the front half 84 and rear half 86 of the outer sheath 26 may be ultrasonically welded together along a longitudinal axis of the sheath, with the radiopaque tip 98 sandwiched between the two halves. The front half 84 and rear half 86 may also be provided with mating recesses and/or grooves to encourage the longitudinal connection. The interior distal tip of the outer sheath 26 and the radiopaque tip 98 may include tongue-and-groove structures (FIG. 15) to further securely attach the outer perimeter of the radiopaque tip to the interior of the outer sheath 26.

According to one aspect of the current disclosure, a method of forming a surgical device may comprise the steps of connecting the cannula 22 and cannula hub 20 (and optionally placing spring 94 around cannula 22), and then ultrasonically connecting the front half 84 and rear half 86 of the insulative sheath 26 together, with the radiopaque tip 98 held in place by the two halves. For example, the cannula assembly 65 may be formed by first selecting the cannula 22. The cannula 22 and cannula hub 20 may then be non-removably attached to each other (such as via press-fit cross pins 68, 70). One half of the insulative sheath, such as front half 84 may be placed around the cannula hub 20, and then the radiopaque tip 98 may be placed at the tip. The second half, such as rear half 86, of the insulative sheath 26 may be placed around the cannula hub 20, holding the distal tip 98 in place. The two halves may then be ultrasonically welded together. In some configurations, in addition to or instead of ultrasonic welding, an adhesive is applied to secure the front half 84 and rear half 86 of the insulative sheath 26. Additionally, an adhesive may be used to secure distal tip 98 in place. In some configurations, distal tip 98 includes threads, and the distal ends of front half 84 and rear half 86 include corresponding threads so that distal tip 98 can be threaded into insulative sheath 26.

Figure 16:
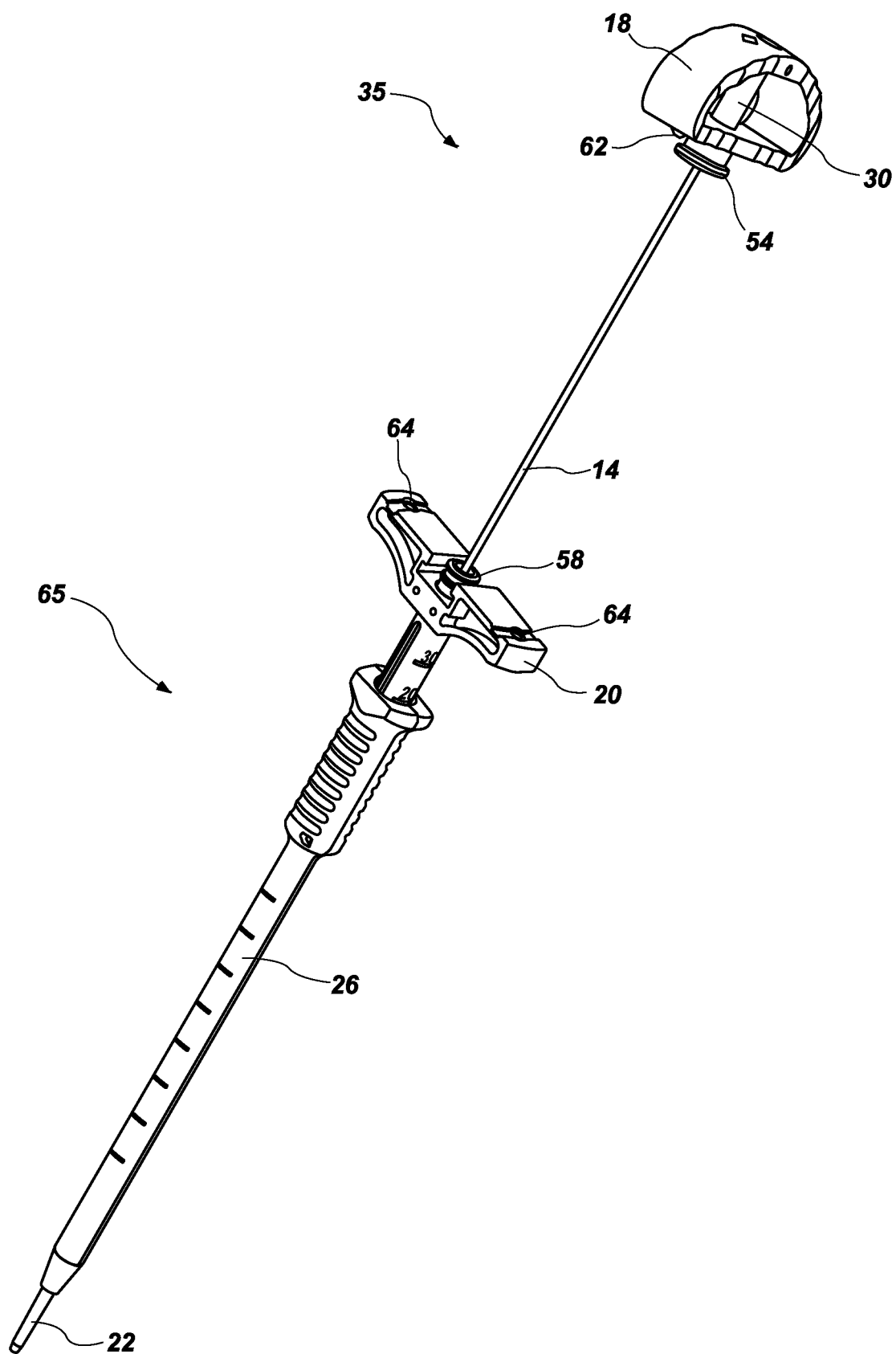
FIG. 16 is a perspective view and FIG. 17 is a front view of the surgical device system of claim 1, with the stylet partially inserted into the cannula.
Figure 17:
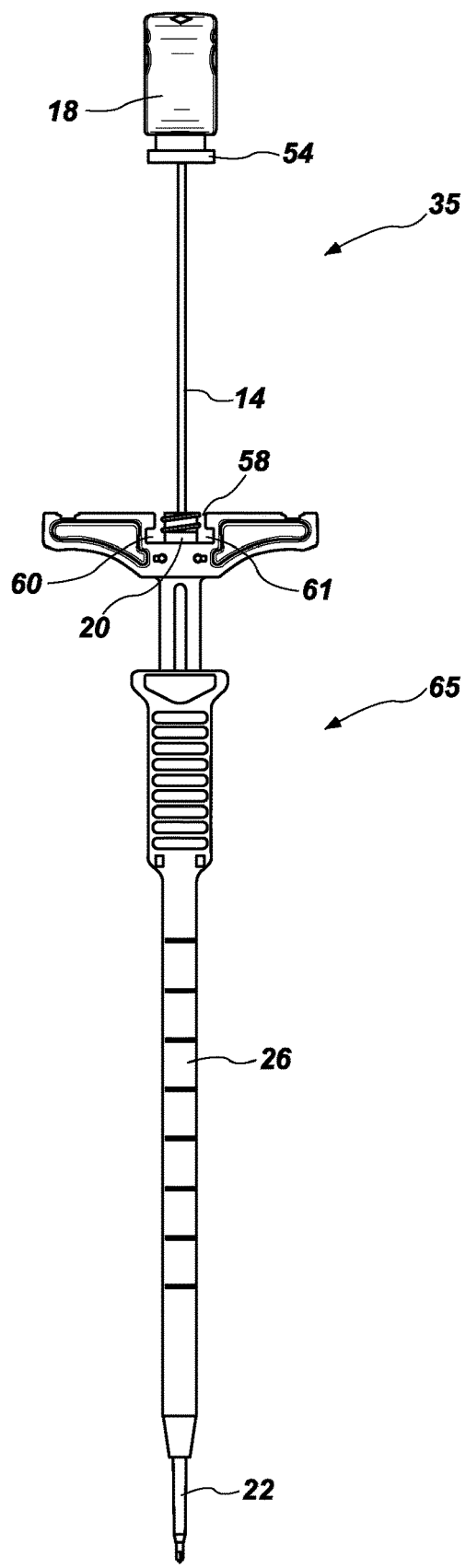
Figure 18:
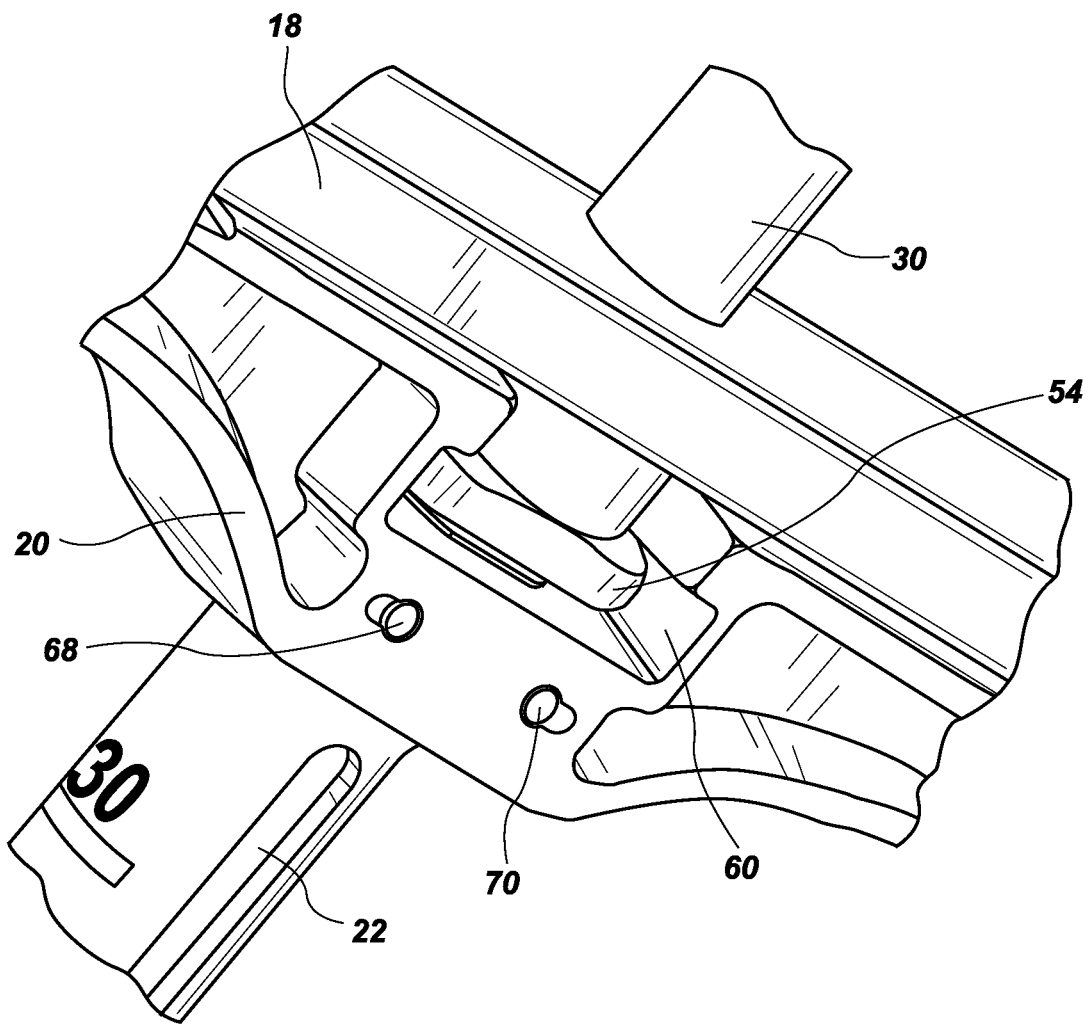
FIG. 18 is a perspective view of a portion of the surgical device system of FIG. 1.

Turning now to FIGS. 16 and 17, the handle assembly 35 is shown partially inserted into the cannula assembly 65. As described above, the flange 56 of the distal projection 54 of the handle extends laterally from the left and right sides (but not the front and back sides), giving the base of the projection 54 has a narrow side from the front to back, and a wider side comprising the flange 56 from the left to right. This allows the handle 18 (or, typically, the entire handle assembly 35) to be turned perpendicularly with respect to the cannula hub 20, the narrow side of the projection 54 to be inserted into a void 58 at the proximal end of the cannula hub 20, and the handle assembly 35 then turned 90 degrees, or parallel with the cannula hub 20. As the handle assembly 35 is turned from a perpendicular to a parallel position with respect to the cannula hub 20, the flange 56 of the handle 18 engages the slots 60, 61 of the void 58 of the cannula hub. The distal side 50 of the handle 18 may also include one or more extensions 62, with corresponding depressions 64 (FIG. 9) or voids in the cannula hub 20. FIG. 18 shows a partial view of the handle assembly 35 connected to the cannula assembly 65, with the flange 56 engaged with the slots 60, 61.

As an example of a method of use of the surgical system disclosed herein, a surgeon may first select a handle assembly 35 having a stylet 14 with the desired geometry. The surgeon may use the geometry tip indicator 52 on the proximal end of the handle assembly 35 to choose the desired geometry. Next, the surgeon may attach the stylet/handle combination (or handle assembly 35) to the cannula assembly 65. More specifically, the distal projection 54 of the handle 18 is connected to the cannula hub 20.

To attach the handle assembly 35 to the cannula hub 20, the stylet 14 is inserted into the interior lumen of the cannula 22 through the proximal end of the cannula hub 20, with the handle turned perpendicularly to the cannula hub (see FIGS. 16-17). The projection 54 on the distal side of the handle is received into the void 58 of the cannula hub. In this position, the lateral flange 56 of the handle is not aligned with the slots 60, 61 of the void 58 of the cannula hub 20. To fully attach the handle assembly 35 to the cannula hub 20, the handle 18 is rotated until the flange 56 is aligned with the slots 60, 61 of the proximal void 58 of the cannula hub 20, or until the handle and cannula hub are parallel, about 90 degrees. As the cannula hub 20 and handle 18 are rotated into alignment, the one or more extensions on the distal side of the handle may also align with the corresponding depressions in the cannula hub thereby at least partially locking handle 18 to the cannula hub 20.

In other configurations, the surgical instrument may be provided to the surgeon pre-assembled, with the handle assembly 35 already attached to the cannula assembly 65. The surgeon need not attach the stylet/handle to the cannula assembly, but need only select a pre-assembled surgical device having the desired distal tip geometry.

After selecting the surgical device with the appropriate distal tip geometry, the surgeon makes an incision in the patient, for example by forming a skin incision and resecting soft tissue disposed over the bone or by using a minimally-invasive technique. The surgeon may then insert the assembled surgical device 10 into the incision, down to the bone. Once bone material is reached, the surgeon may use the distal tip of the stylet 14 to drive the device into the bone. For example, the surgeon may hammer or otherwise provide force to the proximal end 48 of the stylet hub 30. This force may be transferred from the stylet hub 30 to the stylet 14, driving the stylet 14 into bone. The force may also be transferred from the stylet hub 30 to the cannula 22, and drive the cannula 22 into bone. As the cannula is driven into bone, the insulative cannula sheath 26 retracts to remain outside the bone. For example, the insulative cannula sheath 26 may retract by the projections 92 moving proximally within the longitudinal channel 90 of the cannula hub 20.

At any time during the insertion/placement process, the surgeon may visually check the depth of insertion of the instrument into the skin of the patient (from visual depth indicators 102 provided on the outer sheath 26) and also the depth of insertion of the instrument into bone of the patient (from the visual depth indicators 104 provided on the cannula hub 22). It will be appreciated that as the cannula 22 enters bone and the sheath 26 retracts, the proximal end of the sheath 26 will move upward/proximally with respect to the cannula hub 20, moving along the measurement indicators on the cannula hub 20.

Figure 19:
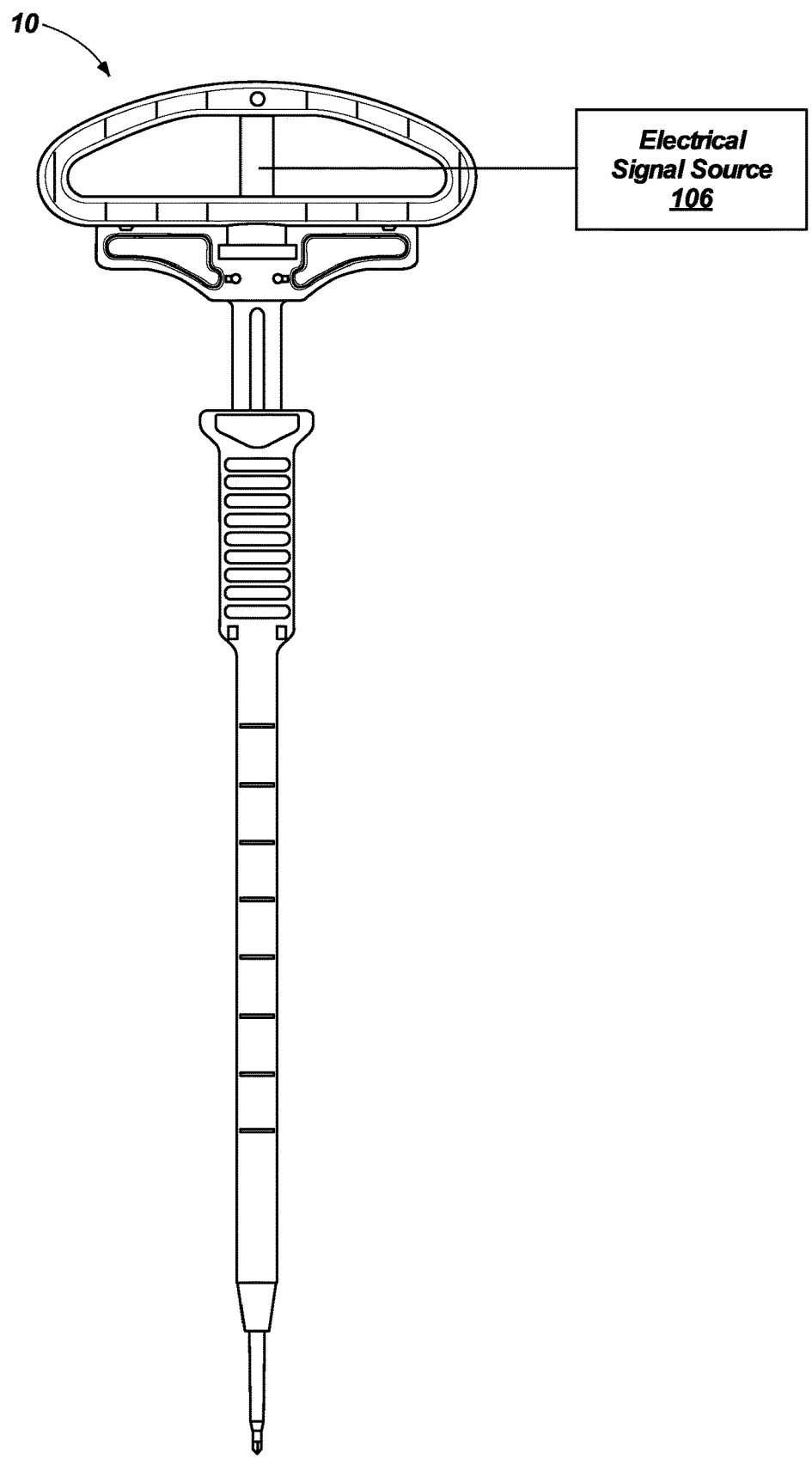
FIG. 19 is a front view of the surgical device system of FIG. 1 coupled to an electrical signal source.

The surgeon may also perform a pedicle integrity test at any time during the insertion process. The pedicle integrity test may be performed by attaching, such as via a clamp, a source of electrical stimulation to the stylet hub (106 in FIG. 19). As electricity is applied to the stylet hub 30, the stylet hub may be in electrical communication with both the stylet 14 and the cannula 22, and electricity may travel along the stylet 14 and cannula 22. The cannula 22 is electrically isolated from surrounding tissue by the outer insulative sheath 26, except for the distal tip that extends past the sheath 26. The insulative sheath 26 prevents unwanted current shunting into surrounding tissues. The surgeon may use the electrical stimulation to determine if the wall of the pedicle has been breached. If a pedicle wall is breached, the stimulation signal applied to the pilot hole via the conductive stylet 14/cannula 22 will cause the various muscle groups coupled to the exiting nerve roots to contract. If the pedicle wall has not been breached, the insulating nature of the pedicle will prevent the stimulation signal from innervating the given nerve roots such that the associated muscle groups will not twitch.

After the surgeon is satisfied with the formation of the pilot hole, the surgeon may remove the handle assembly 35 (which includes the stylet 14) from the cannula assembly 65. The surgeon may rotate the handle assembly 35 about 90 degrees with respect to the cannula hub 20 such that the flange 56 of the handle disengages the slots 60, 61 of the cannula hub 20. With the handle assembly 35 perpendicular to the cannula hub 20, the handle assembly 35, including the stylet 14, may be pulled away from the cannula hub, and the stylet 14 removed from the inner cannula 22. Typically the cannula 22 is left in place and other surgical tools may be inserted into the cannula 22 as necessary.

According to aspect A, a surgical tool system may comprise: a conductive stylet comprising a shaft extending from a distal end to a proximal end, the distal end advanceable into bone material, and the proximal end comprising a conductive stylet hub; a handle non-removably attached to the conductive stylet hub, the handle comprising a proximal gripping portion, and the handle removably attachable to a proximal end of an insulative cannula hub; the insulative cannula hub non-removably attached to a conductive cannula; the conductive cannula surrounding the conductive stylet when the handle is attached to the proximal end of the insulative cannula hub; and an outer, elongated insulative sheath slideably engaged to insulative cannula hub, the outer, elongated insulative sheath further comprising a tip on a distal end formed of radiopaque material.

Aspect B comprises the surgical tool system of aspect A, the conductive stylet hub comprising a stylet hub diameter, and the conductive cannula comprising a cannula diameter, the stylet hub diameter being at least as large as the cannula diameter. Aspect C comprises the surgical tool system of aspects A or B, the conductive cannula surrounding the conductive stylet when the insulative cannula hub is attached to the handle. Aspect D comprises the surgical tool system of any of aspects A through C, the handle further comprising a distal connecting portion, the conductive stylet hub receivable within a longitudinal void extending through the proximal gripping portion and distal connecting portion.

Aspect E comprises the surgical tool system of any of aspects A through D, the handle further comprising a projection on the distal connecting portion, the projection comprising a laterally extending flange; and the insulative cannula hub comprising a proximal void and one or more slots, the projection on the distal connecting portion of the handle receivable within the proximal void and the laterally extending flange receivable within the one or more slots. Aspect F comprises the surgical tool system of any of aspects A through E, wherein the conductive stylet is integral to the handle. Aspect G comprises the surgical tool system of any of aspects A through F, wherein the outer, elongated insulative sheath comprises a front half and a back half, the front half and back half ultrasonically welded together along a longitudinal axis of the outer, elongated insulative sheath.

Aspect H comprises the surgical tool system of any of aspects A through G, wherein the conductive cannula comprises a proximal diameter tapering to a distal diameter, the distal diameter smaller than the proximal diameter. Aspect I comprises the surgical tool system of any of aspects A through H, wherein the conductive stylet further comprises a geometry at its distal tip, and the handle further comprises a geometry indicator at a proximal end of the handle.

Aspect J comprises the surgical tool system of any of aspects A through I, wherein the conductive stylet hub surrounds the proximal end of the conductive stylet. Aspect K comprises the surgical tool system of any of aspects A through J, wherein the handle further comprises a proximal end and a distal end, with a void extending longitudinally through the proximal end and the distal end, the conductive stylet hub passing through the void in the proximal end and distal end. Aspect L comprises the surgical tool system of aspect K, wherein a proximal end of the conductive stylet hub is exposed through the proximal end of the handle.

Aspect M comprises the surgical tool system of any of aspects A through L, the insulative cannula hub further comprising markings indicating a length of the conductive stylet extending beyond the outer, elongated insulative sheath. Aspect N comprises the surgical tool system of any of aspects A through M, the elongated insulative sheath further comprising markings indicating a depth of penetration of the surgical tool system. Aspect O comprises the surgical tool system of any of aspects A through N, the insulative cannula hub further comprising a longitudinal channel having a first groove and a second groove, and the outer, elongated insulative sheath further comprising an extension slideable within the longitudinal channel.

Aspect P comprises the surgical tool system of any of aspects A through O, the conductive stylet hub coupleable to an electrical source to transmit an electrical current from the electrical source to the conductive stylet hub. Aspect Q comprises the surgical tool system of any of aspects A through P, wherein the conductive cannula is comprised of entirely conductive material.

Aspect R discloses a surgical tool system comprising: a handle assembly, the handle assembly comprising: a conductive stylet comprising a shaft extending from a distal end to a proximal end, the distal end advanceable into bone material, and the proximal end comprising a conductive stylet hub; a handle non-removably attached to the conductive stylet hub, the handle comprising a proximal gripping portion and a distal connecting portion, the handle having a longitudinal void extending through the proximal gripping portion and distal portion for snugly receiving the conductive stylet hub, and the handle removably attachable to a proximal end of an insulative cannula hub, the handle further comprising a projection on the distal connecting portion, the projection comprising a laterally extending flange; and a cannula assembly non-removably attachable to the handle assembly, the cannula assembly comprising: the insulative cannula hub non-removably attached to a cannula, the insulative cannula hub comprising a proximal void, and one or more slots, the projection on the distal connecting portion of the handle receivable within the proximal void and the laterally extending flange receivable within the one or more slots; the cannula surrounding the conductive stylet when the handle is attached to the proximal end of the insulative cannula hub; and an outer, elongated insulative sheath slideably engaged to insulative cannula hub; the outer, elongated insulative sheath further comprising a tip on a distal end formed of radiopaque material.

While the present surgical device has been specifically described with respect to use in pedicle integrity assessments, it will be appreciated that other applications are possible and contemplated herein. The various aspects described above, including elements of the various embodiments described above, can be combined to provide further embodiments. Various portions and components of apparatus within the scope of this disclosure, including for example, structural components, can be formed by one or more various suitable manufacturing processes known to those in the art. Similarly, various portions and components of apparatuses within the scope of this disclosure can be made from suitable materials known to those in the art.

The above description has set out various features, functions, methods, and other aspects of the disclosure. Time and further development may change the manner in which the various aspects are implemented. The scope of protection defined by the claims is not intended to be limited to the specific sizes, shapes, features, or other aspects of the disclosed embodiments. The claimed inventions may be implemented or embodied in other forms while still being within the scopes of the concepts disclosed hereby. Also included are equivalents of the elements of the claims that can be made without departing from the scopes of concepts properly protected by the claims that follow.

What is claimed:

1. A surgical tool system comprising:
   a conductive stylet comprising a shaft extending from a distal end to a proximal end, the distal end advanceable into bone material, and the proximal end receivable within a conductive stylet hub;
   a handle non-removably attached to the conductive stylet hub, the handle comprising a proximal gripping portion, and the handle removably attachable to a proximal end of an insulative cannula hub, wherein when the handle is removed from the proximal end of the insulative cannula hub, the conductive stylet hub is also removed;
   the insulative cannula hub non-removably attached to a conductive cannula;
   the conductive cannula surrounding the conductive stylet when the handle is attached to the proximal end of the insulative cannula hub; and
   an outer, elongated insulative sheath slideably engaged to insulative cannula hub, the outer, elongated insulative sheath further comprising a tip on a distal end formed of radiopaque material.

2. The surgical tool system of claim 1, the conductive stylet hub comprising a stylet hub diameter, and the conductive cannula comprising a cannula diameter, the stylet hub diameter being at least as large as the cannula diameter.

3. The surgical tool system of claim 1, the conductive cannula surrounding the conductive stylet when the insulative cannula hub is attached to the handle.

4. The surgical tool system of claim 1, the handle further comprising a distal connecting portion, the conductive stylet hub receivable within a longitudinal void extending through the proximal gripping portion and distal connecting portion.

5. The surgical tool system of claim 4, the handle further comprising a projection on the distal connecting portion, the projection comprising a laterally extending flange; and the insulative cannula hub comprising a proximal void and one or more slots, the projection on the distal connecting portion of the handle receivable within the proximal void and the laterally extending flange receivable within the one or more slots.

6. The surgical tool system of claim 1, wherein the conductive stylet is integral to the handle.

7. The surgical tool system of claim 1, wherein the outer, elongated insulative sheath comprises a front half and a back half, the front half and back half ultrasonically welded together along a longitudinal axis of the outer, elongated insulative sheath.

8. The surgical tool system of claim 1, wherein the conductive cannula comprises a proximal diameter tapering to a distal diameter, the distal diameter smaller than the proximal diameter.

9. The surgical tool system of claim 1, wherein the conductive stylet further comprises a geometry at its distal tip, and the handle further comprises a geometry indicator at a proximal end of the handle.

10. The surgical tool system of claim 1, wherein the conductive stylet hub surrounds the proximal end of the conductive stylet.

11. The surgical tool system of claim 1, wherein the handle further comprises a proximal end and a distal end, with a void extending longitudinally through the proximal end and the distal end, the conductive stylet hub passing through the void in the proximal end and distal end.

12. The surgical tool system of claim 11, wherein a proximal end of the conductive stylet hub is exposed through the proximal end of the handle.

13. The surgical tool system of claim 1, the insulative cannula hub further comprising markings indicating a length of the conductive stylet extending beyond the outer, elongated insulative sheath.

14. The surgical tool system of claim 1, the elongated insulative sheath further comprising markings indicating a depth of penetration of the surgical tool system.

15. The surgical tool system of claim 1, the insulative cannula hub further comprising a longitudinal channel having a first groove and a second groove, and the outer, elongated insulative sheath further comprising an extension slideable within the longitudinal channel.

16. The surgical tool system of claim 1, the conductive stylet hub coupleable to an electrical source to transmit an electrical current from the electrical source to the conductive stylet hub.

17. The surgical tool system of claim 1, wherein the conductive cannula is comprised of entirely conductive material.

18. The surgical tool system of claim 1, wherein an electrical source is connectable to the conductive stylet hub when the handle is removably attached to the proximal end of an insulative cannula hub, the electrical source to conduct electricity from the electrical source, through the conductive stylet hub to the conductive stylet and conductive cannula, and wherein the electrical source cannot be connected to the conductive stylet hub to conduct electricity from the electrical source through the conductive cannula when the handle is removed from the proximal end of the insulative cannula hub.

19. The surgical tool system of claim 1, wherein the handle has a first position attached to the proximal end of the insulative cannula hub, and a second position wherein the handle is removed from the proximal end of the insulative cannula hub; and wherein, in the first position, an electrical source if coupled to the conductive stylet hub can conduct electricity through the conductive cannula, and in the second position the electrical source if coupled to the conductive stylet hub cannot conduct electricity through the conductive cannula.

* * * * *